United States Patent [19]

Earle et al.

[11] Patent Number: 5,289,727
[45] Date of Patent: Mar. 1, 1994

[54] BULK MATERIAL SAMPLING DEVICE

[75] Inventors: Anthony Earle, Harrow Weald; David J. Young, Chorleywood, both of England

[73] Assignee: Eastman Kodak Company, Rochester, N.Y.

[21] Appl. No.: 760,431

[22] Filed: Sep. 16, 1991

[30] Foreign Application Priority Data

Nov. 16, 1990 [GB] United Kingdom ................. 9024993

[51] Int. Cl.⁵ .............................................. G01N 1/08
[52] U.S. Cl. .............................. 73/864.45; 73/864.63; 73/864.64
[58] Field of Search ........... 73/864.44, 864.45, 864.74, 73/864.63, 864.64; 175/20, 58

[56] References Cited

U.S. PATENT DOCUMENTS

| | | | |
|---|---|---|---|
| 215,230 | 5/1879 | Lyman | 73/864.64 |
| 230,121 | 7/1880 | Frost | 73/864.64 |
| 323,057 | 7/1885 | Meylor | 73/864.64 |
| 715,631 | 12/1902 | Ayres | 73/864.44 |
| 902,049 | 10/1908 | Bonnell | 73/864.64 |
| 1,027,246 | 5/1912 | Granville | 73/864.44 |
| 1,256,413 | 2/1918 | Wiswell | 73/864.64 |
| 2,688,877 | 9/1954 | Peine | 73/864.64 |
| 2,896,444 | 7/1959 | Forman et al. | 73/864.64 |
| 3,383,131 | 5/1968 | Rosfelder | 73/864.44 |
| 4,172,385 | 10/1979 | Cristensen | 73/864.63 |
| 4,283,946 | 8/1981 | Bowser et al. | 73/864.64 X |
| 4,383,583 | 5/1983 | Baker | 175/20 |

FOREIGN PATENT DOCUMENTS

| | | | |
|---|---|---|---|
| 531833 | 12/1957 | Belgium | 73/864.44 |
| 257850 | 11/1969 | U.S.S.R. | 73/864.64 |

*Primary Examiner*—Tom Noland
*Attorney, Agent, or Firm*—Clyde E. Bailey

[57] ABSTRACT

A sampling device comprising an outer tube and an inner tube that is eccentrically mounted for rotation within the outer tube, the inner and outer tubes being disposed in spaced, parallel relationship so that relative rotation therebetween cuts a sample of bulk material and retains that sample for subsequent removal.

7 Claims, 2 Drawing Sheets

BULK MATERIAL SAMPLING DEVICE

BACKGROUND OF THE INVENTION

This invention relates generally to sampling devices, and particularly to sampling devices that remove a core of material from bulk material.

2. Description of the Prior Art

Sampling devices for sampling grain and other materials are known. U.S. Pat. No. 2,896,444, No. 2,688,877, No. 902,049, No. 323,057, No. 230,121, and No. 215,230 disclose grain sampling devices.

In particular, U.S. Pat. No. 2,896,444, No. 2,688,877, No. 902,049, No. 323,057, and No. 230,121 disclose devices that comprise two concentric tube portions, an outer tube portion and an inner tube portion that is rotatable relative to the outer tube portion. Both tube portions have formed in them apertures which, when they are aligned, allow ingress of material into the device and which, when they are not aligned, retain that material in the device for extraction from the bulk material.

Other sampling devices are disclosed in U.S. Pat No. 4,383,583, No. 4,172,385, No. 3,383,131, and No. 1,027,246. U.S. Pat. No. 4,383,583 discloses a soil sampling tool which comprises a hollow tube having a pointed closure at its lower end for soil penetration and a handle at its upper end for manipulation of the tool. A lateral opening is provided adjacent to the lower end to allow soil to enter the tube and fall into a ladle mounted therein. The tool is removed from the soil before the soil sample is removed therefrom using the ladle.

U.S. Pat. No. 4,172,385 discloses a sampling device for use in septic tanks. That device comprises a transparent tube having an external parallel rod which carries a closure plate. The tube is inserted into the tank and the plate is swung into a position against the lower open end of the tube to retain the sample. The plate is retained in position by a spring.

U.S. Pat. No. 3,383,131 discloses a core sampler in the form of a hollow tube having a removable liner and a cutter at its lower end. The sample is retained in the liner by means of a flexible tube portion which closes above the cutter to retain the sample as the device is lifted from its sampling position.

U.S. Pat. No. 1,027,246 discloses a device that is used to obtain samples from peat bogs. The device comprises a hollow tube, within which is mounted a plunger. The plunger is lifted to a first position within the tube to receive a plug of the material being sampled. If the plug is relatively dry, the plug is retained in the tube by frictional resistance. .If the plug is wet, the plunger is moved to a second position so that a vacuum is created in the tube to retain the plug.

In each case discussed above, the sampling device is removed from the bulk material as a whole, that is, none of the prior-art devices allows the sample to be removed from the device prior to removing the device itself from the bulk material. Also, in many cases the sample breaks up during its removal from the device, or during insertion of the device into the bulk material.

Furthermore, none of the devices discussed above can be used to remove a representative core of material from bulk material which is in a firm set state but which can be cut readily by a blade.

SUMMARY OF THE INVENTION

It is therefore an object of the present invention to provide a sampling device which both cuts a sample from bulk material and allows it to be removed in one piece, that is, a device that allows the sample to remain continuous and undamaged so that any stratification present in the sample can be retained for analysis.

According to one aspect of the present invention, a sampling device is provided comprising:

an outer tube having a nose portion for penetrating material to be sampled;

at least one aperture formed in the nose portion; and at least one inner tube mounted within the outer tube for receiving material to be sampled;

each inner tube being movable relative to the outer tube between a first position, in which the inner tube is aligned with a respective one of the apertures, and a second position, in which the inner tube is closed by the nose portion;

characterized in that each inner tube is mounted eccentrically within the outer tube.

By the foregoing eccentric arrangement of the inner and outer tubes, a continuous sample can be obtained and removed from bulk material without having to withdraw the outer tube of the sampling device from the material.

Furthermore, that eccentricity between the inner and outer tubes provides a cutting means for detaching the sample from the surrounding bulk material.

BRIEF DESCRIPTION OF THE DRAWINGS

For a better understanding of the present invention, reference is now made to the accompanying drawings, in which.

DESCRIPTION OF THE PREFERRED EMBODIMENT

Figure 1:
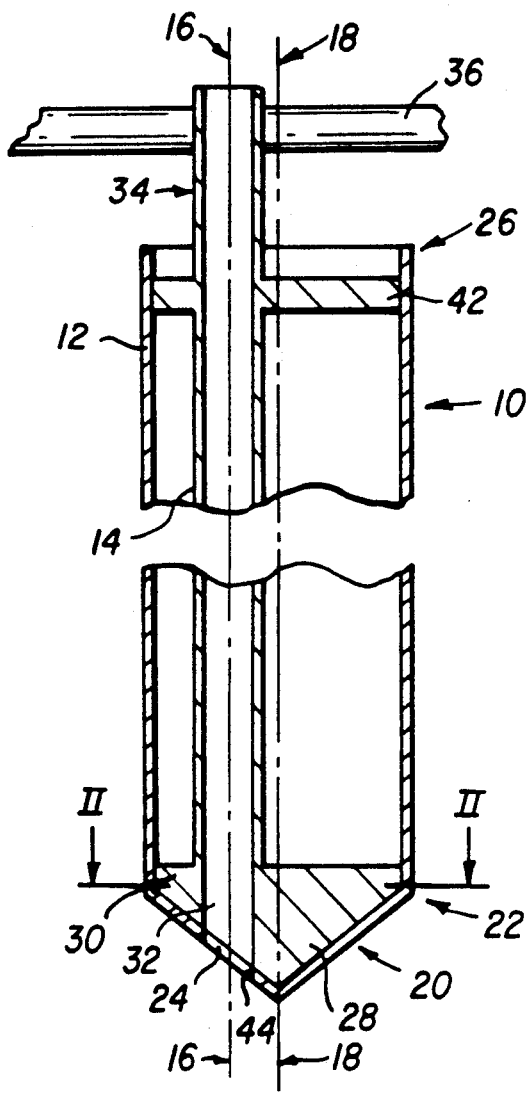
FIG. 1 is a sectioned side elevation of a sampling device in a first position (prior to and during insertion of the device into a material to be sampled)

A sampling device 10 constructed in accordance with the present invention is shown in the drawings. Referring to FIGS. 1-4, the device 10 comprises an outer tube 12 and a removable inner tube 14. Inner tube 14 is eccentrically mounted within outer tube 12 so that the longitudinal axis 16 of inner tube 14 is always spaced from, but parallel to, the longitudinal axis 18 of outer tube 12.

Outer tube 12 has a conical nose portion 20 formed at one end 22. Nose portion 20 is hollow and has a hole 24 formed in it. Hole 24 is offset from axis 18 of outer tube 12. Outer tube 12 is open at its other end 26 to allow insertion and removal of tube 14.

Inner tube 14 also has a conical nose portion 28, formed at one end 30, which sits in nose portion 20 of tube 12. When portion 28 is pushed against portion 20, a seal is formed. A hole 32 is formed in nose portion 28 and is aligned with longitudinal axis 16 of inner tube 14 so as to allow a continuous sample to be taken from bulk material.

Figures 5, 6:
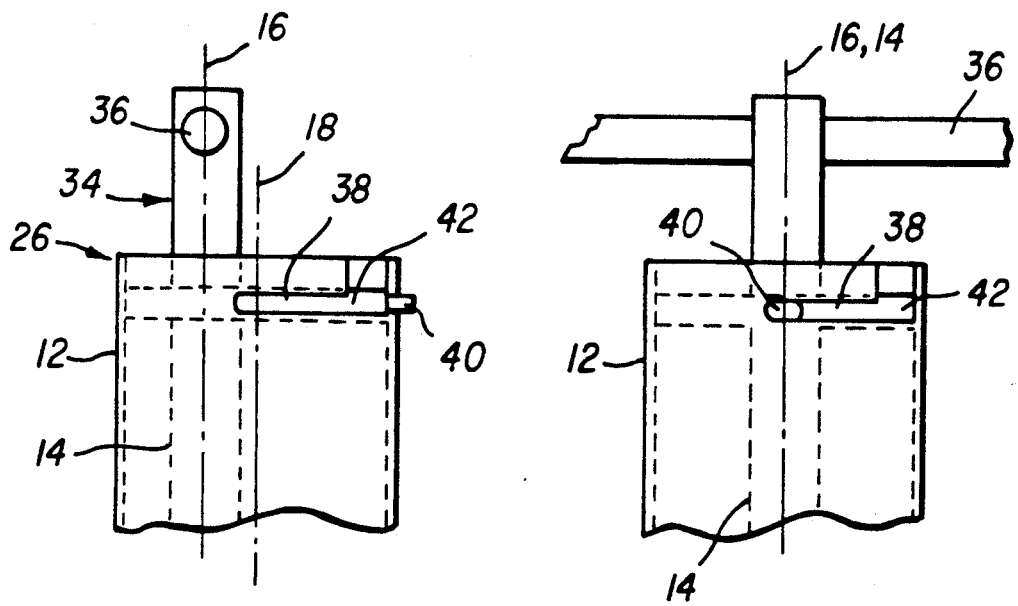
FIGS. 5 and 6 are partial side elevations corresponding to FIGS. 1 and 3 respectively, illustrating operation of detent means formed on a sampling device constructed in accordance with the present invention, the detent means being used to lock the inner and outer tubes together for insertion into bulk material.

At the other end 34 of inner tube 14, a handle 36 is provided, which assists with insertion of device 10 into bulk material and subsequent removal of inner tube 14 containing a sample core from outer tube 12. So that handle 36 can be used for insertion of device 10, a detent 38 is formed in the outer tube wall, adjacent to open end 26 of the outer tube, as shown in FIGS. 5 and 6. Detent 38 cooperates with a spigot 40 carried by a support plate 42 mounted on inner tube 14 adjacent to handle 36. Spigot 40 is engaged with detent 38 for both inserting device 10 into and, if necessary, removing it from bulk material.

Figure 2:
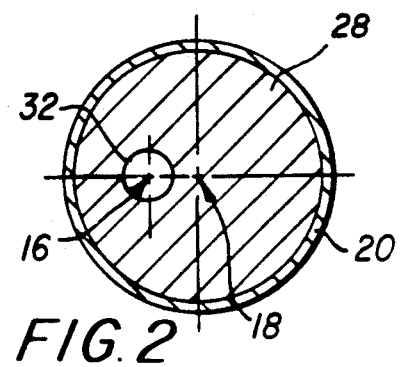
FIG. 2 is a sectioned view taken along lines II—II in FIG. 1.
Figure 3:
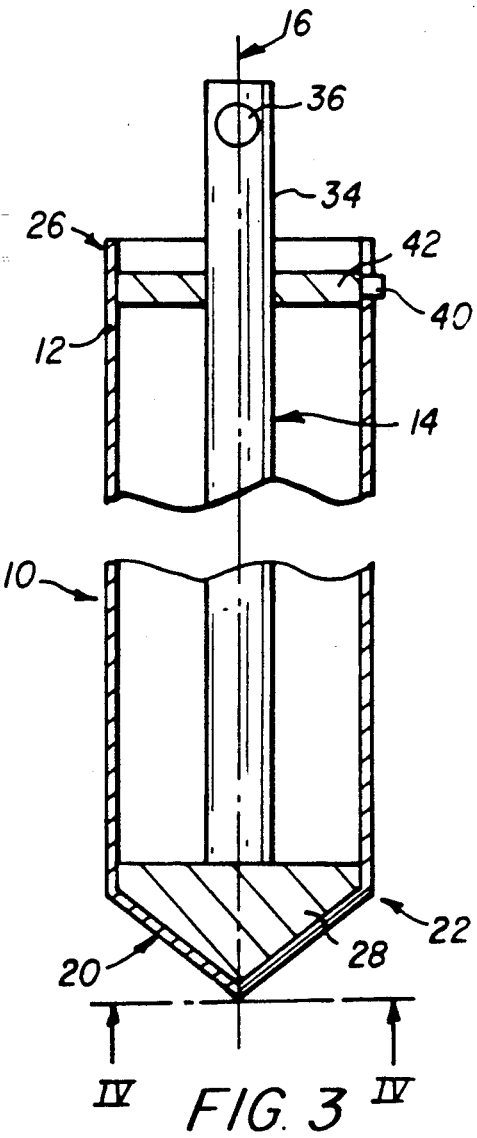
FIG. 3 is a sectioned side elevation of the sampling device in a second position (prior to withdrawal of the device from the material being sampled)
Figure 4:
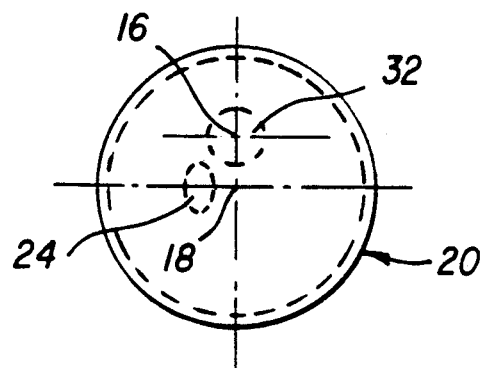
FIG. 4 is a bottom plan view taken along lines IV—IV in FIG. 3.

As shown in FIGS. 1 and 2, holes 24 and 32 are aligned as device 10 is inserted into bulk material for sampling. Nose portions 20 and 28 are aligned to form a cutting edge 44. As device 10 is pushed into bulk material, cutting edge 44 penetrates the material and forces a core of material (not shown) into inner tube 14. In this position, spigot 40 is retained in detent 38 as shown in FIG. 5.

For cutting of a sample core and subsequent removal of inner tube 14, once the required depth has been reached, handle 36 is rotated to a position wherein hole 32 is no longer aligned with hole 24 (see FIGS. 3 and 4) and wherein nose portion 28 of inner tube 14 closes hole 24 in outer tube 12. In this position, as shown more clearly in FIG. 6, spigot 40 is no longer retained in detent 38, and inner tube 14 containing the sample core can be removed from outer tube 12 using handle 36. The sample core is retained in inner tube 14 by friction.

After the sample core has been removed from inner tube 14, with the aid of a ramrod if necessary, the inner tube can be reinserted into the outer tube and turned so that spigot 40 is again retained in detent 38. Outer tube 12 can then be removed from the bulk material using handle 36 on inner tube 14.

It is to be noted that outer tube 12 can easily be removed as the hollow inner tube 14 allows free passage of air to the deepest point, thereby overcoming any suction effects.

If desired, more than one sample could be taken at a time. For example, two or more inner tubes 14 could extend between nose portion 28 and support plate 42, each tube 14 having a hole 32 in nose portion 28 which corresponds to a respective hole 24 in nose portion 20 of outer tube 12.

Although the angle of relative rotation between inner tube 14 and outer tube 12 is shown to be approximately 90°, other angles are equally applicable. The necessary criterion is that the angle of relative rotation be sufficient to allow closure of hole 24 to cut off the sample from its bulk material.

A separate handle (not shown) may be provided on outer tube 12 so that the outer tube can be removed from the bulk material after inner tube 14 containing the sample has been removed. In that case, detent 38 and spigot 40 would not be needed, and there would be no need to reinsert inner tube 14 in order to remove device 10.

A sampling device according to this invention could be manufactured in a range of sizes depending on the sizes of the samples required.

We claim:

1. A sampling device comprising:
   an outer tube including, at one end thereof, a nose portion for penetrating material to be sampled, said nose portion having at least one aperture therein; and
   at least one inner tube mounted within said outer tube for receiving the material to be sampled, each said at least one inner tube having at least one further aperture positioned eccentrically to said outer tube, the mounting being such that, except for the nose portion, in any cross sectional plane normal to central longitudinal axes of each tube and containing cross sections of each tube, the cross section of the at least one inner tube is completely within the cross-section of the outer tube;
   each of said at least one inner tube being movable relative to said outer tube between a first position, wherein said at least one further aperture of each of said at least one inner tube is aligned with a respective one of said at least one aperture, and a second position, wherein said at least one further aperture of each of said at least one inner tube is closed by said nose portion.

2. A device as claimed in claim 1 wherein said each of said at least one inner tube is adapted to be removed from said outer tube.

3. A device as claimed in claim 1 wherein said each of said at least one inner tube is of circular cross section.

4. A device as claimed in claim 1 wherein said at least one inner tube comprises a single inner tube only.

5. A device as claimed in claim 1 wherein said each of said at least one inner tube is connected to a support plate at another end of said outer tube remote from said one end thereof.

6. A device as claimed in claim 5 wherein said support plate includes a spigot thereon, wherein said outer tube includes a detent therein, and wherein said spigot cooperates with said detent to lock said outer tube and said at least one inner tube together, to thereby facilitate inserting said device into, and removing it from, the material to be sampled.

7. A device as claimed in claim 1 wherein said at least one inner tube is mounted eccentrically within said outer tube.

* * * * *